United States Patent
Ambeck-Madsen et al.

(10) Patent No.: US 12,102,431 B2
(45) Date of Patent: Oct. 1, 2024

(54) SYSTEM AND METHOD FOR DETERMINING THE PERCEPTUAL LOAD AND THE LEVEL OF STIMULUS PERCEPTION OF A HUMAN BRAIN

(71) Applicants: TOYOTA MOTOR EUROPE, Brussels (BE); UCL BUSINESS LTD, London (GB)

(72) Inventors: Jonas Ambeck-Madsen, Brussels (BE); Nilli Lavie, London (GB); Merit Bruckmaier, London (GB); Ilias Tachtsidis, London (GB)

(73) Assignees: TOYOTA JIDOSHA KABUSHIKI KAISHA, Toyota (JP); UCL BUSINESS LTD, London (GB)

( * ) Notice: Subject to any disclaimer, the term of this patent is extended or adjusted under 35 U.S.C. 154(b) by 996 days.

(21) Appl. No.: 17/054,189

(22) PCT Filed: May 25, 2018

(86) PCT No.: PCT/EP2018/063809
§ 371 (c)(1),
(2) Date: Nov. 10, 2020

(87) PCT Pub. No.: WO2019/223880
PCT Pub. Date: Nov. 28, 2019

(65) Prior Publication Data
US 2021/0153792 A1    May 27, 2021

(51) Int. Cl.
*A61B 5/18* (2006.01)
*A61B 5/00* (2006.01)
(Continued)

(52) U.S. Cl.
CPC ........ *A61B 5/14553* (2013.01); *A61B 5/0048* (2013.01); *A61B 5/14546* (2013.01); *A61B 5/18* (2013.01); *A61B 5/4064* (2013.01)

(58) Field of Classification Search
CPC .......... G09B 23/28; A61B 5/18; A61B 5/1455
See application file for complete search history.

(56) References Cited

U.S. PATENT DOCUMENTS 11,717,686 B2 *  8/2023  Poltroak ............... A61N 1/0551
                                                           600/14
2008/0065468 A1 *  3/2008  Berg ..................... G06Q 30/02
                                                           705/7.32
(Continued)

FOREIGN PATENT DOCUMENTS

CN  102715889 B   1/2014
CN  107788970 A   3/2018
(Continued)

OTHER PUBLICATIONS

Sophie Schwartz et al, "Attentional Load and Sensory Competition in Human Vision: Modulation of fMRI Responses by Load at Fixation during Task-irrelevant Stimulation in the Peripheral Visual Field", Cerebral Cortex, vol. 15, Issue 6, Jun. 2005, pp. 770-786. (Year: 2004).*

(Continued)

*Primary Examiner* — Kurt Fernstrom
(74) *Attorney, Agent, or Firm* — Oliff PLC (57) ABSTRACT

A method of determining the perceptual load of a human brain. The perceptual load is induced by a predetermined task carried out by the human. The method includes the steps of: measuring with a functional near-infrared spectroscopy (fNIRS) sensor device a metabolic activity of the human brain while the task is carried out and determining the perceptual load as a function of a measured change in metabolic activity. The invention further relates to a method of determining the level of stimulus perception corresponding systems.

21 Claims, 4 Drawing Sheets

(51) Int. Cl.
 *A61B 5/145* (2006.01)
 *A61B 5/1455* (2006.01)

(56) References Cited

U.S. PATENT DOCUMENTS

| | | | |
|---|---|---|---|
| 2008/0275340 A1* | 11/2008 | Beach | A61B 8/0808 |
| | | | 600/438 |
| 2009/0163777 A1* | 6/2009 | Jung | A61B 5/0533 |
| | | | 600/301 |
| 2009/0299160 A1* | 12/2009 | Moridaira | A61B 5/6814 |
| | | | 600/322 |
| 2018/0075772 A1* | 3/2018 | Carr | G09B 19/00 |
| 2018/0257682 A1* | 9/2018 | Brooks | B61L 3/006 |
| 2021/0153792 A1* | 5/2021 | Ambeck-Madsen | |
| | | | A61B 5/0048 |

FOREIGN PATENT DOCUMENTS

| | | |
|---|---|---|
| JP | 2007-061484 A | 3/2007 |
| JP | 2007-183824 A | 7/2007 |
| JP | 2011-010714 A | 1/2011 |

OTHER PUBLICATIONS

Jan. 25, 2022 Office Action issued in Japanese Patent Application No. 2020-565947.

Miya, M. "Effect of the Perceptual Load in the Selective Attention— What is the Perceptual Load?," Kyoto University Graduate School of Education Bulletin, [online] vol. 46, Kyoto University Graduate School of Education, Mar. 31, 2000, pp. 183-195, Internet <URL http://hdl.handle.net/2433/57370>.

Phan, P. et al., "Spatial Distribution of Changes in Oxidised Cytochrome C Oxidase During Visual Stimulation Using Broadband Near Infrared Spectroscopy Imaging," Advances in Experimental Medicine and Biology, 2016, pp. 195-201.

Schwartz, S. et al., "Attentional Load and Sensory Competition in Human Vision: Modulation of fMRI Responses by Load at Fixation during Task-irrelevant Stimulation in the Peripheral Visual Field," Cerebral Cortex, Sep. 30, 2004, vol. 15, No. 6, pp. 770-786.

Translation of Apr. 11, 2023 Office Action issued in Japanese Patent Application No. 2022-101049.

Nilli Lavie, "Distracted and confused?: Selective attention under load" Trends in Cognitive Sciences, vol. 9, No. 2, pp. 76-82, 2005.

Bertram Wortelen et al., "Towards the Integration and Evaluation of Online Worload Measures in a Cognitive Architecture", 7th IEEE International Conference on Cognitive Infocommunications, pp. 000011-000016, Oct. 16-18, 2016.

Zhen Zhang et al., "Passive BCI Based on Sustained Attention Detection: An fNIRS Study", pp. 220-227, 2016.

Sophie Schwartz et al., "Attentional Load and Sensory Competition in Human Vision: Modulation of fMRI Responses by Load at Fixation during Task-irrelevant Stimulation in the Peripheral Visual Field" Cerebral Cortex, vol. 15, No. 6, Jun. 2005.

Feb. 4, 2019 Internaitonal Search Report issued in International Patent Application No. PCT/EP2018/063809.

\* cited by examiner

SYSTEM AND METHOD FOR DETERMINING THE PERCEPTUAL LOAD AND THE LEVEL OF STIMULUS PERCEPTION OF A HUMAN BRAIN

FIELD OF THE DISCLOSURE

The present disclosure is related to a system and method for determining the perceptual load for a human brain, in particular a perceptual load caused by a predetermined task carried out by the human, e.g. the task of driving a vehicle. The present disclosure is further related to a system and method for determining the level of perception of a stimulus of a second type by a human brain, in particular of an unattended stimulus while the human carries out a predetermined task, e.g. driving a vehicle.

BACKGROUND OF THE DISCLOSURE

The ability to recognise perceptual load of an uncontrollable dynamic visual environment and changes hereof including unattended events could significantly improve safety (e.g. driving safety) by providing the basis for new designs and strategies for use of warning signals. It could also set a standard against which the usefulness of other measures of detecting a human's attention and engagement can be assessed, e.g. physiological measures such as pupil or EEG measurements. Further it could also apply to designing optimum strategies for machine-to-human (e.g. vehicle-to-driver) interactions for highly automated systems (e.g. vehicles), for example but not limited to the case of so-called take-over-requests, where the automatic control system requests a driver to re-take control over vehicle operation.

Not all information that hits the eye's retina is perceived. Whether information is perceived or not will depend on the strength of the neural signal in the visual cortex (striate and extrastriate cortices). It is also established that people may not perceive information outside the focus of their attention ("looking but not seeing") if the attended information is of high perceptual load i.e. during carrying out a highly demanding task). These effects of "looking but not seeing" are known to be a major cause of accidents (e.g. car and aeroplane crashes etc.).

The human's capacity for processing perceptual information is limited The level of perceptual load in task processing is hence an important factor in determining what stimuli may be perceived. When perceptual load is high, for example when the visual scene is crowded, or more demanding perceptual decisions have to be made, stimuli that are outside of the focus of attention are less likely to be noticed since no spare attentional capacity is available for their processing. In extreme cases this can lead to the phenomenon of inattentional blindness (or deafness) where participants entirely fail to perceive a stimulus due to the lack of perceptual resources, cf.:

Cartwright-Finch U, Lavie N (2007) The role of perceptual load in inattentional blindness. Cognition 102:321-340.

On the other hand, under conditions of low load, when spare capacity is available it automatically 'spills over' to the perception of task-irrelevant stimuli which increases their potential to act as distractors, cf.:

Forster S, Lavie N (2008) Failures to ignore entirely irrelevant distractors: The role of load. J Exp Psychol Appl 14:73-83.

fMRI has been used to measure the impact of perceptual load of attended task processing on the vascular response (BOLD response) to unattended stimuli, cf. e.g.:

Rees G, Frith C D, Lavie N (1997) Modulating irrelevant motion perception by varying attentional load in an unrelated task. Science 278:1616-1619, Schwartz S, Vuilleumier P, Hutton C, Maravita A, Dolan R J, Driver J (2005) Attentional load and sensory competition in human vision: modulation of fMRI responses by load at fixation during task-irrelevant stimulation in the peripheral visual field. Cereb cortex 15:770-786, and Torralbo A, Kelley T A, Rees G, Lavie N (2016) Attention induced neural response trade-off in retinotopic cortex under load. Sci Rep 6:33041.

However, fMRI is not a portable, wearable technique and therefore does not allow the same applications as fNIRS which exists as a wearable system. EEG systems have been used to measure the impact of perceptual load on the brain response to unattended stimuli (cf. Parks N A, Beck D M, Kramer A F (2013): Enhancement and suppression in the visual field under perceptual load. Front Psychol 4:275). However, EEG is highly sensitive to participant movements and although portable, its setup is rather cumbersome (e.g. application of conductive gel to the head is required in some system configurations). It is therefore less suited to practical application outside laboratory environments.

Several studies used commercial fNIRS to measure blood oxygenation and deoxygenation levels ($HbO_2$ and HHb) in response to cognitive factors that indirectly relate to perceptual load. $HbO_2$ and HHb have been shown to be related to the level of visual-motor demand, cf.:

Hosseini S M H, Bruno J L, Baker J M, Gundran A, Harbott L K, Gerdes J C, Reiss A L (2017) Neural, physiological, and behavioral correlates of visuomotor cognitive load. Sci Rep 7:8866, and related to cognitive load, cf.:

Fishburn F A, Norr M E, Medvedev A V., Vaidya C J (2014) Sensitivity of fNIRS to cognitive state and load. Front Hum Neurosci 8:76.

Both types of load do not relate to perceptual load that can lead the effect of 'looking but not seeing' (often termed "inattentional blindness"). Zhang et al, 2016 and Kojima and Suzuki, 2010 relate the levels of $HbO_2$ and HHb to attentional demand in a task, however their attentional demand manipulations were not shown to constitute perceptual load that would be expected to lead to inattentional blindness, as shown in cognitive neuroscience research of perceptual load. They are not teching to measure metabolism either.

Harasawa and Shiori, 2011 found a difference in $HbO_2$ between conditions of tracking in one disc and two discs but only when presented unilaterally not bilaterally. This research did not address perceptual load leading to inattentional blindness either, cf.:

Harasawa M, Shioiri S (2011) Asymmetrical brain activity induced by voluntary spatial attention depends on the visual hemifield: A functional near-infrared spectroscopy study. Brain Cogn 75:292-298.

Both fMRI and the commercially available fNIRs deduce about neural activity indirectly from measures of blood oxygenation levels. One study used fMRI measuring the blood oxygenation levels and blood flow to estimate (not measure) the metabolic rate of oxygen in the visual cortex based on a model approximating other physiological variables with a constant for attended and unattended stimulus conditions, cf.:

Moradi F, Buracas G T, Buxton R B (2012) Attention strongly increases oxygen metabolic response to stimulus in primary visual cortex. Neuroimage 59:601-607.

Heekeren et al, 1999 and Phan et al, 2016a used broadband fNIRs developed to measure neural activity more directly by detecting the oxidation levels of the cytochrome-c oxidase enzyme (OxCCO) in the mitochondria which are prevalent in the neural cells and indicate the level of neural oxygen metabolism. They related the relative OxCCO levels to the presence of visual stimulation, cf.:

Heekeren H R, Kohl M, Obrig H, Wenzel R, von Pannwitz W, Matcher S J, Dirnagl U, Cooper C E, Villringer A (1999) Noninvasive assessment of changes in cytochrome-c oxidase oxidation in human subjects during visual stimulation. J Cereb Blood Flow Metab 19:592-603, and Phan P, Highton D, Brigadoi S, Tachtsidis I, Smith M, Elwell C E (2016a) Spatial Distribution of Changes in Oxidised Cytochrome C Oxidase During Visual Stimulation Using Broadband Near Infrared Spectroscopy Imaging. In: Advances in Experimental Medicine and Biology, pp 195-201.

Kolyva et al, 2012 and Phan et al, 2016b showed that the level of oxCCO in the prefrontal cortex is influenced by cognitive tasks (e.g. performance of an anagram solving task vs rest), cf.:

Kolyva C, Tachtsidis I, Ghosh A, Moroz T, Cooper C E, Smith M, Elwell C E (2012) Systematic investigation of changes in oxidized cerebral cytochrome c oxidase concentration during frontal lobe activation in healthy adults. Biomed Opt Express 3:2550-2566, and Phan P, Highton D, Lai J, Smith M, Elwell C, Tachtsidis I (2016b) Multichannel multi-distance broadband near-infrared spectroscopy system to measure the spatial response of cellular oxygen metabolism and tissue oxygenation. Biomed Opt Express 7:4424.

While the neural correlates of perceptual load have been investigated in many studies using a range of neuroimaging techniques, the source of the capacity limitation remains to be understood.

SUMMARY OF THE DISCLOSURE

Currently, it remains desirable to provide a system and method for determining the perceptual load of a human brain. Furthermore it remains desirable to provide a system and method for determining a level of stimulus perception of a human brain, in particular when the human brain perceives (i.e. is exposed to and/or receives signals from) an unattended stimuli while the human is carrying out a predetermined task (e.g. a driving task).

More in particular, it is desirable to have a portable non-invasive system that can detect the level of perception of an unattended stimulus during driving (or carrying out another expected task), especially that is not as sensitive to motion as the current EEG based systems. Such a system allows for a better understanding of driver states during driving and in and as such can better inform the development of assistive car technology, compared with current systems that use EEG.

As already pointed out, Heekeren et al, 1999 and Phan et al, 2016a related the level of oxCCO in the visual cortex to the presence of visual stimulation. Kolyva et al, 2012 and Phan et al, 2016b showed that the level of oxCCO in the prefrontal cortex is influenced by cognitive tasks (e.g. performance of an anagram solving task vs rest). However none of these publications relate to the cognitive neuroscience of attention, perception, and (more specifically) of perceptual load, and cannot be applied to measuring and detecting perceptual load: for this expertise in cognitive neuroscience of attention is required. On the other hand, the techniques used in cognitive neuroscience cannot measure the neural metabolism (instead, they are restricted to the more indirect measurement of Blood oxygenation and deoxygenation levels ($HbO_2$, HHb). Measuring neural metabolism has though the advantage that it is a more direct indicator of neural activity and could thus provide a faster response to any change in the neural activity as compared to the oxygenation and deoxygenation ($HbO_2$ and HHb) measures, in the existing fNIRS sensor devices which rely on the delayed vascular haemodynamic response.

Therefore, according to the embodiments of the present disclosure, the present disclosure relates to a method of determining the perceptual load of a human brain. The perceptual load is induced by a predetermined (or predefined) task carried out by the human (e.g. a driving task or another non-driving tasks while the car is driven in autonomous mode, e.G. watching a movie). The method comprises the steps of:

measuring with a functional near-infrared spectroscopy (fNIRS) sensor device a metabolic activity of the human brain while the task is carried out, and determining the perceptual load as a function of a measured change in metabolic activity.

By providing such a method, a mobile, motion-resilient (in particular real-time or quasi realtime) measurement of cognitive conditions, including so-called perceptual load, is possible.

The predetermined task may comprise a varying complexity inducing a correspondingly varying perceptual load.

Said complexity may also be referred to as a perceptual complexity. In particular, the predetermined task may comprise predetermined (or predefined) varying levels of perceptual load.

Generally, in case the metabolic activity is changing for more than a predetermined amount, in relation to changes of perceptual load in the task it may be determined that the human brain is still able to perceive and/or keep control of the task. In other words, a significant change that relates to the task changes of load may indicate that the human brain is still able to perceive and/or keep control of the task.

In case e.g. the complexity increases and at the same time the measured change in metabolic activity does not exceed a predetermined (or predefined) first upper threshold, it may be determined that the perceptual load induced by the predetermined task exceeds a perceptual load threshold and/or that the human brain was not attentive to the task.

The threshold is desirably predetermined in the sense that it is expressed by a predetermined value or that it is predetermined by the brain capacity itself. In another aspect, the predetermined threshold may be predetermined by the brain perceptual load capacity but said predetermined threshold is desirably lower than a maximum load capacity of the human brain.

Accordingly, a case, where the perceptual load is determined to exceed the predetermined threshold, it may be followed that the perceptual load exceeds the human brain's capacity and/or even an inattentional blindness/deafness for the task.

For example, in such a case a precautionary action could be taken, e.g. triggering any alarm signals or activating an automated driving system taking over driving control.

In case the complexity decreases and at the same time the measured change in metabolic activity does not exceed a predetermined (or predefined) first lower threshold, it may be determined that the human brain was not attentive to the task.

It may hence be determined whether the human pays attention to a task (and is not drowsy), even in the case that said task has a decreased complexity. Carrying out such a low complex task may also be referred to as a baseline activity. If the human is however not attentive to the task, there is no metabolic response corresponding to said task. In other words, the metabolic activity does not exceed a predetermined (or predefined) first lower threshold.

An example might be a vehicle passenger (intended to be the driver) who is watching the driving scene during autonomous driving. Said driving scene may provide an empty or relatively empty road, i.e. a task with decreased complexity. With the present disclosure it is possible to check, whether the passenger pays attention to occurrences in the driving scene, e.g. road signs. If there is not determined a metabolic activity exceeding a predetermined (or predefined) first lower threshold when an occurrence happens (e.g. passing a road sign), it may be determined that the passenger is not attentive to the driving scene.

In case the complexity decreases and at the same time the measured change in metabolic activity does not decrease below a predetermined (or predefined) first upper threshold, it may be determined that the human brain was not attentive to the task.

If the complexity is reduced and the human (e.g. the driver) brain is engaged in the task, the human's brain metabolic activity is expected to be lower too. If it remains higher it may mean the human's brain is engaged in a different task—e.g. the driver brain engaged in a non-driving task. In general if there are changes in complexity beyond a certain threshold and the changes in metabolic activity do not pass a certain threshold too then it may be determined that the human brain was not attentive to the task.

Accordingly, a case where the perceptual load is too low may lead to an auto process task irrelevant stimuli (i.e. to automatic processing of task irrelevant stimuli). For example the human brain may concentrate on anything else and not pay sufficient attention to the task anymore. The result may be again an inattentional blind/deafness for the task.

For example, in such a case a precautionary action could be taken, e.g. triggering any alarm signals to "waken up" the human, i.e. draw his/her attention back to the task.

The present disclosure further relates to a method of determining the level of perception of a stimulus of a second type by a human brain. The method comprises the steps of:
  in a first time period exposing the human brain to a predetermined (or predefined) stimulus of a first type, in response to which the human carries out a predetermined (or predefined) task, thereby inducing a perceptual load in the human brain,
  in a second time period exposing the human brain to a predetermined (or predefined) stimulus of the first type and in addition to a predetermined (or predefined) stimulus of a second type perceivable by the human brain,
  measuring with a functional near-infrared spectroscopy (fNIRS) sensor device a metabolic activity of the human brain in the first and the second time period, and
  determining the level of perception of the stimulus of the second type as a function of a measured change in metabolic activity in the second time period in relation to the first time period.

Said determined level of perception may imply both the (positive) case of actually perceiving the stimulus of the second type, as well as the opposite, not perceiving anything of the second stimulus in spite of it being in the field of view (case of looking, but failing to see). For example, in case the level of perception is e.g. "0" there may be determined that there is no perception. In case it is e.g. "100", there may be determined a perception.

The first and second time may have any order and length. They may also be repeated several times.

The load measurement may be understood as continuous, as long as there are times with a stimulus of a second type and times without said stimulus of a second type.

Generally, the method of determining the level of perception of a stimulus of a second type may be combinable with any aspect of the method of determining the perceptual load of a human brain.

The predetermined task may be a driving task. It is noted that according to the present disclosure a driving task is understood as being predetermined (or predefined) in the sense as it comprises types of predetermined tasks, as. e.g. steering, accelerating, braking, etc. Furthermore, also the stimuli to which the human has to respond, in order to carry out the driving task, are predetermined, i.e. expected stimuli, as e.g. turns of the road, other vehicles, etc.

The first type may be a task-primary type, and the second type may be a task-secondary type.

In other words, the task to be carried out may primarily depend on the stimulus of the first type (i.e. stipulated by the task-primary type stimulus). The stimulus of the second type may have no influence on the task to be carried out and/or may only require a sudden but timely limited reaction. In an example, the task could be driving (e.g. "driving home after work") and the task-secondary stimulus type could be the sudden appearance of a pedestrian. For example, in case the pedestrian is not crossing the street, it is possible that its appearance does not influence the driving task. Anyway, it is a relevant precautionary measure that the driver notices the pedestrian.

In a further example, in the context of autonomous driving, the task could be watching a movie in the vehicle, the stimulus of the first type the displayed movie and the stimulus of the second type could be the sudden appearance of a pedestrian or any other occurrence in the driving scene outside the vehicle. For example, it is possible the automated driving system of the vehicle may react autonomously on the occurrence. Anyway, it may be a precautionary measure to check whether the vehicle passenger notices (and/or intended driver) the occurrence, as well.

In case the measured change in metabolic activity in the second time period in relation to the first time period exceeds a predetermined (or predefined) (second upper) threshold, it may be determined that the level of perception of the stimulus of the second type exceeds a predetermined minimum perception level.

For example, in such a case no precautionary action would need to be taken, e.g. triggering any alarm signals or activating an automated driving system taking over driving control.

In case the measured change in metabolic activity in the second time period in relation to the first time period does not exceed a predetermined (or predefined) threshold, it may be determined that the human brain does not perceive the stimulus of the second type and/or that the human brain did not attend to the stimulus of the second type.

For example, in such a case a precautionary action could be taken, e.g. triggering any alarm signals or activating an automated driving system taking over driving control.

The method may further comprise the steps of: generating the predetermined task to be carried out by the human and/or sensing the predetermined task carried out by the human.

For example, in case of an experimental test the predetermined task can be completely generated. Also in case of a driving task the task may be partly be generated/influenced by the motion (e.g. speed and direction) of the vehicle. Anyway, in case of a driving task, said task may be sensed, e.g. using different sensors, e.g. optical sensors and a speed sensor etc.

The method may further comprise the step of exposing the human brain to a predetermined (or predefined) stimulus of a first type, in particular comprising a driving scene, in response to which the human carries out a predetermined (or predefined) task, in particular comprising a driving task.

The stimulus of the first type may be attended by the human when carrying out the task.

For example, in case the task to be carried out is a driving task, the stimulus of the first type may be an attended stimulus of a driving scene, e.g. a turn of the road, in respond to which the human has to carry out a steering task.

The stimulus of the second type may be not predetermined by the task such that it is an unattended stimulus for the human when carrying out the task.

For example, in case the task to be carried out is a driving task, the stimulus of the second type may be an unattended stimulus of a driving scene, e.g. a football rolling across the road.

The overall energy consumption of the brain is known to be essentially constant and the bioenergetic cost of neural spiking is high, necessitating an efficient use of the available resources. The inventors have found that the increase in energy consumption associated with the additional processing requirements of a high load (vs. low load) task leaves less metabolic resources for the processing of unattended stimuli.

Stimuli of the first type may be variable (i.e. may vary) such that the complexity of the predetermined task varies correspondingly.

The present disclosure further relates to a system for determining the perceptual load of a human brain. The system comprises:
a functional near-infrared spectroscopy (fNIRS) sensor device configured to measure a change in metabolic activity of the human brain, and
a control device configured to determine the perceptual load based on the measured change in metabolic activity.

Generally, the described system may comprise one or more system features corresponding to the method features described above, in particular of the method of determining the perceptual load of a human brain.

The perceptual load may be induced by a predetermined (or predefined) task carried out by the human.

The system may further comprise a generating and/or sensoring device configured to generate a predetermined (or predefined) task to be carried out by the human and/or sense a predetermined (or predefined) task carried out by the human.

The present disclosure further relates to a system for determining the level of perception of a stimulus by a human brain. The system comprises: a generating and/or sensoring device configured to:
in a first and in a second time period generate a predetermined (or predefined) task to be carried out by the human and/or sense a predetermined (or predefined) task carried out by the human,
in the second time period generate and/or sense a predetermined (or predefined) stimulus perceivable by the human brain,
a functional near-infrared spectroscopy (fNIRS) sensor device configured to measure a metabolic activity of the human brain in the first and the second time period, and
a control device configured to determine the level of perception of the stimulus as a function of a measured change in metabolic activity in the second time period in relation to the first time period.

Said stimulus desirably corresponds to the "stimulus of a second type" in the method cited above. Generally, the described system may comprise one or more system features corresponding to the method features described above, in particular of the method of determining the level of perception of a stimulus of a second type by a human brain.

Furthermore, said system may also be the described system for determining the perceptual load of a human brain, or it may be combinable with the latter.

The generating and/or sensoring device may be configured to generate and expose the human brain to a predetermined stimulus of a first type, in response to which the human has to carry out a predetermined (or predefined) task.

Alternatively or additionally, the generating and/or sensoring device may be configured to sense the predetermined (or predefined) task carried out by the human.

A broadband functional near-infrared spectroscopy (fNIRS) sensor device may be used to test changes in metabolic activity. The sensor device may be configured to monitor the redox state changes of cytochrome c oxidase (oxCCO), a mitochondrial enzyme indicative of cellular oxygen metabolism, in addition to the concentration changes of oxygenated ($HbO_2$) and deoxygenated haemoglobin (HHb).

The increase in energy requirements during neuronal activation is mostly covered by oxidative phosphorylation in the mitochondria. Measuring of oxCCO activity therefore enables to monitor changes in metabolic activity which are associated with the increase in energy consumption during neural responses. The present disclosure enables to directly compare the metabolic activity elicited by optically identical stimuli under different levels of perceptual load.

The functional near-infrared spectroscopy (fNIRS) sensor may be configured to measure redox state changes of a mitochondrial enzyme indicative of cellular oxygen metabolism, in particular cytochrome c oxidase (oxCCO).

The control device may be configured to determine the perceptual load based on the measured redox state changes the measured mitochondrial enzyme indicative of cellular oxygen metabolism, in particular of cytochrome c oxidase (oxCCO).

The measured changes in metabolic activity may indicate an increase in energy consumption during neural responses of the human brain.

The functional near-infrared spectroscopy (fNIRS) sensor may further be configured to measure the concentration changes of oxygenated ($HbO_2$) and/or of deoxygenated haemoglobin (HHb).

The control device may be configured to pre-select regions of interest of the brain based on the measured concentration changes of oxygenated ($HbO_2$) and/or of deoxygenated haemoglobin (HHb), and determine the perceptual load based on the measured changes in metabolic activity in said pre-select regions of interest of the brain.

The functional near-infrared spectroscopy (fNIRS) sensor device may be configured to measure changes in metabolic activity in the medial occipital lobe and/or the right medial occipital gyrus of the human brain.

The control device may be configured to determine the perceptual load based on the measured changes in metabolic activity in the medial occipital lobe and/or the right medial occipital gyrus.

The sensor device may be a broadband functional near-infrared spectroscopy (fNIRS) sensor device, e.g. configured to sense in the range of 650 nm to 900 nm.

For example, a broadband fNIRS sensor device for the head may be used to establish a new way to measure and detect the strength of brain signals ($HbO_2$, HHb, oxCCO) in identifying over the visual cortex both the level of perceptual load in an attended task and the response to an unattended stimulus.

Broadband fNIRS may measure the cerebral metabolism through the cytochrome c oxidase redox state (oxCCO) as well as levels of blood oxygenation and deoxygenation ($HbO_2$ and HHb).

The metabolism measure is directly related to neural response, while $HbO_2$ and HHb being measures of the vascular response can only indirectly lead to conclusions about neural response.

The desired metabolism response is unavailable in any conventional fNIRS to date because they use only 2-3 wavelengths rather than broadband.

The measurement of reduced metabolism desirably indicates an unattended stimulus during carrying out a task implying an increased load compared to reduced load attended task conditions. Initial analysis of new data indicates also increased metabolism in response to attended stimuli.

The sensor device may comprise a plurality of sources and a plurality of detectors configured to provide a plurality of measurement channels across the occipital lobe of the brain.

The measurement channels may be spread over the outer extents of the primary visual cortex (V1) and/or across the extrastriate areas (V2, V3, and V4) of the brain.

The measurement channels may be grouped into a plurality of regions of interest of the brain, in particular including the left/right inferior occipital gyrus (IOG), the left/right middle occipital gyrus (MOG), and/or the medial occipital lobe.

It is generally noted that determination according to the disclosure, e.g. "determination of the perceptual load", may also be regarded as an estimation, as the determined result might not be exact (e.g. in view of the real driving scene).

The disclosure further relates to a vehicle comprising a control device as described above.

The vehicle may further comprise a sensor configured to sense the visual driving scene and/or the driver face, in particular the eyes/pupils, the sensor being in particular an optical sensor, more in particular at least one digital camera. The driving scene may be the stimulus of the first type.

The vehicle may be configured for a at least partially automated driving control. The control device may be used in a pre-processing step of the driving control to identify situations implying an increased perceptual load for the driver.

The vehicle may comprise hardware and/or software resources configured for the at least partially automated driving control.

The vehicle may comprise a human-machine-interface configured to inform the human about critical situation, e.g. with regard to an increased perceptual load. Accordingly, the human-machine-interface may contribute to a safe driving of the driver.

Additionally or alternatively, the human-machine-interface may be configured for so-called take-over-requests, where the automatic control system requests a driver to re-take control over vehicle operation. In such situations it is important for the automatic control system to be able to reliably determine the perceptual load of the driving scene related to the driving task. A further exemplary configuration would be that the automatic control system takes over driving control, e.g. in case the system recognizes that the determined perceptual load exceeds a specific threshold.

It is intended that combinations of the above-described elements and those within the specification may be made, except where otherwise contradictory.

It is to be understood that both the foregoing general description and the following detailed description are exemplary and explanatory only and are not restrictive of the disclosure, as claimed.

The accompanying drawings, which are incorporated in and constitute a part of this specification, illustrate embodiments of the disclosure and together with the description, and serve to explain the principles thereof.

DESCRIPTION OF THE EMBODIMENTS

Reference will now be made in detail to exemplary embodiments of the disclosure, examples of which are illustrated in the accompanying drawings. Wherever possible, the same reference numbers will be used throughout the drawings to refer to the same or like parts.

Figure 1:
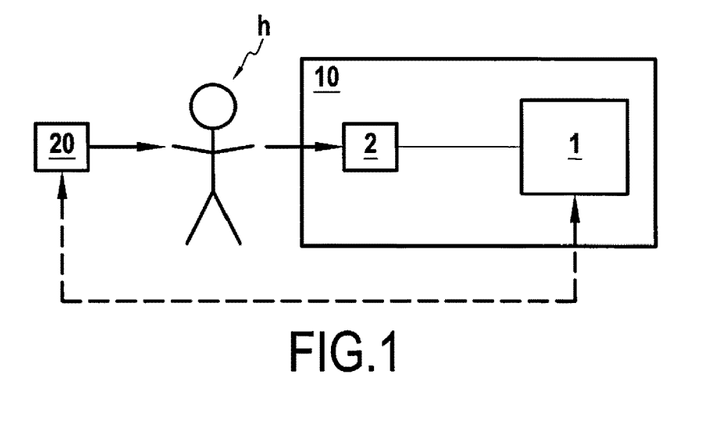
FIG. 1 shows a block diagram of a system with a control device according to embodiments of the present disclosure.

FIG. 1 shows a block diagram of a system 10 with a control device (or electronic device) 1 according to embodiments of the present disclosure.

The control device 1 may be connected to or comprises data storage (not shown). Said data storage may be used to store algorithms to determine the perceptual load or the level of stimulus perception, as described below.

The control device 1 may additionally carry out further functions in the system 10. For example, the control device may also act as the general purpose ECU (electronic control unit) of the system. The control device 1 may comprise an electronic circuit, a processor (shared, dedicated, or group), a combinational logic circuit, a memory that executes one or more software programs, and/or other suitable components that provide the described functionality.

The control device 1 is further connected to a fNIR sensor device 2. The control device 1 and the sensor device 2 may be comprised by a system 10. The fNIR sensor device may be a functional near-infrared spectroscopy. It is desirably further broadband sensor, e.g. in the range of 650 nm to 900 nm (i.e. from red light to near-infrared light). In this context a band is a wavelength of light so broadband is referring to a broad (large) number of wavelengths of light. Meanwhile e.g. the Shimadzu LightNIRS system uses three bands of light, the sensor device 10 preferably uses several hundreds of bands of light.

The fNIR sensor device 2 may measure the redox state changes of a mitochondrial enzyme indicative of cellular oxygen metabolism, in particular cytochrome c oxidase (oxCCO).

The fNIR sensor device 2 is configured such that it measure the metabolic activity of the brain of a human h. The sensor device may especially take measurements at the visual cortex, more in particular of the outer extents of the primary visual cortex (V1) and across the extrastriate areas (including V2, V3, and V4)

The fNIRS device may comprise four sources and 10 detectors (arranged as rows of 5 detectors, 4 sources, 5 detectors), resulting in a total of 16 measurement channels across the human's occipital lobe. The optodes may be placed according to the 10-20 electrode system and the location of all positions may be digitised to allow to map channel locations on a standardised brain. Based on the anatomical areas associated with average MNI coordinates, the measurement channels may be grouped into 5 regions of interest: left/right inferior occipital gyrus (IOG), left/right middle occipital gyrus (MOG), and medial occipital lobe (based on the AAL digital brain atlas). Functionally, this means the channels are desirably spread over the outer extents of the primary visual cortex (V1) and across the extrastriate areas (including V2, V3, and V4). The setup may be any other configuration to over the occipital cortex, or over other cortical areas associated with attention and perception for example parietal cortex and auditory temporal cortex.

Preferred regions of interest (ROI) for the occipital cortex are the left middle occipital gyrus (MOG); medial occipital lobe; right MOG; and/or right inferior occipital gyrus (IOG).

Examples of suitable anatomical locations are indicated in the following table of average MNI coordinates for each channel:

| Channel | X | Y | Z | ROI |
|---|---|---|---|---|
| 1 | −54.7292 | −76.1875 | 12.3125 | Left medial occipital gyrus |
| 2 | −43.375 | −89.0208 | 16.7708 | Left medial occipital gyrus |
| 3 | −51.3125 | −80.2708 | −6.3958 | Left inferior occipital gyrus |
| 4 | −42.2917 | −92.2917 | −2.9167 | Left medial occipital gyrus |
| 5 | −28.875 | −97.8542 | 18.3958 | Left medial occipital gyrus |
| 6 | −12.9792 | −103.896 | 19.0625 | Medial occipital lobe |
| 7 | −28.25 | −102.604 | −0.14583 | Left medial occipital gyrus |
| 8 | −13.9792 | −107.771 | 1.625 | Left medial occipital gyrus |
| 9 | 7.1667 | −100.917 | 17.1458 | Medial occipital lobe |
| 10 | 24 | −101.542 | 15.9375 | Medial occipital lobe |
| 11 | 6.3958 | −102.688 | 1.5 | Medial occipital lobe |
| 12 | 22.7917 | −104.938 | −1.9583 | Right inferior occipital gyrus |
| 13 | 39.2292 | −92.125 | 13.0417 | Right medial occipital gyrus |
| 14 | 52.9375 | −79.1042 | 9.5208 | Right medial occipital gyrus |
| 15 | 37.5 | −95.5 | −6 | Right inferior occipital gyrus |
| 16 | 48.5208 | −83.4375 | −10.625 | Right inferior occipital gyrus |

The system 10 is further connected or even comprises a generating and/or sensing device 20. Said device 20 is configured to generate and/or sense stimuli to which the human h is exposed. Accordingly, in case the device 20 is configured as a stimulus generator, the system 10, in particular the control device 1 controls the device 20. In case the device 20 is configured as a stimulus sensor, the system 10, in particular the control device 1 receives sensor data of the device 20. Also a combined configuration of the device 20 as a generator and sensor is possible.

With regard to the stimuli, any kinds of stimuli are possible, as long as they are perceivable by the human brain. Examples for basic stimuli area described below in context with FIG. 4, where the system 10 mainly serves as an experimental test system.

However, the system may also be employed in real-life applications, e.g. in a vehicle. In this case the stimulus of a first type (as explained later in more detail) may consist e.g. of the visual and dynamic driving scene which is perceivable by a driver (i.e. the human h).

The generating and/or sensing device 20 may comprise a sensor configured to sense the visual driving scene, the sensor being in particular an optical sensor, more in particular at least one digital camera.

Accordingly, also a plurality of sensors may be used, in order to sense (i.e. perceive) the driving scene. For example, two sensors might be used, in order to obtain three dimensional information of the driving scene, as well as surround view type sensor configuration, and any combination hereof.

The sensor data of the device 20 may then be provided to the system 10, in particular the control device 1.

Furthermore the stimulus of a second type (as explained later in more detail) may consist e.g. of a predetermined event in the visual and dynamic driving scene, e.g. a person passing or approaching the driving lane. In this case the stimulus of a second type may be sensed (e.g. in the same way as the stimulus of the first type) and identified by the device 20 and a respective information may be provided to the system 10. Alternatively the control device may receive the sensor output of the device 20 and identify on its own the stimulus of a second type, e.g. based on a machine learning technique.

The stimulus of a second type may also consist of a stimulus generated by the device 20, e.g. a predetermined sound or light signal, and which is perceivable by the driver. In this case the system 10, in particular the control device 1 may control the output of the device 20.

The generating or sensing device 20 may further be configured to instruct the human to carry out a specific task in response to the perception of a stimulus of the first type. This case is in particular relevant in an experimental scenario, e.g. in that of FIG. 4.

Alternatively, the device may determine a task implied (i.e. provided) by a stimulus of a first type. This case is in particular relevant for a real life application, e.g. in a driving vehicle. In this example, the stimulus of a first type may be the driving scene and accordingly, the related task may comprise driving the vehicle.

For example, the driving scene may imply a braking (task). In this case the task to be carried out by the driver depends on the driving scene, i.e. the (sensed) stimulus of the first type. In another example, the device 20 may determine based on a scheduled destination that the driver has to leave the current road and has to carry out a left or right turn, crossing lanes of traffic (higher perceptual load) or empty lanes (lower perceptual load) to reach the new road. In this case the task to be carried out by the driver depends on the driving scene, i.e. the (sensed) stimulus of the first type, and on an external instruction provided to the driver. To summarize, the task may be context dependent.

In the following it is explained in more detail in the context of FIG. 2 and FIG. 3 the functioning of the control device 1, in particular how the received sensor data from the fNIR sensor device 2 and the generating or sensing device 20 are proceeded.

Figure 2:
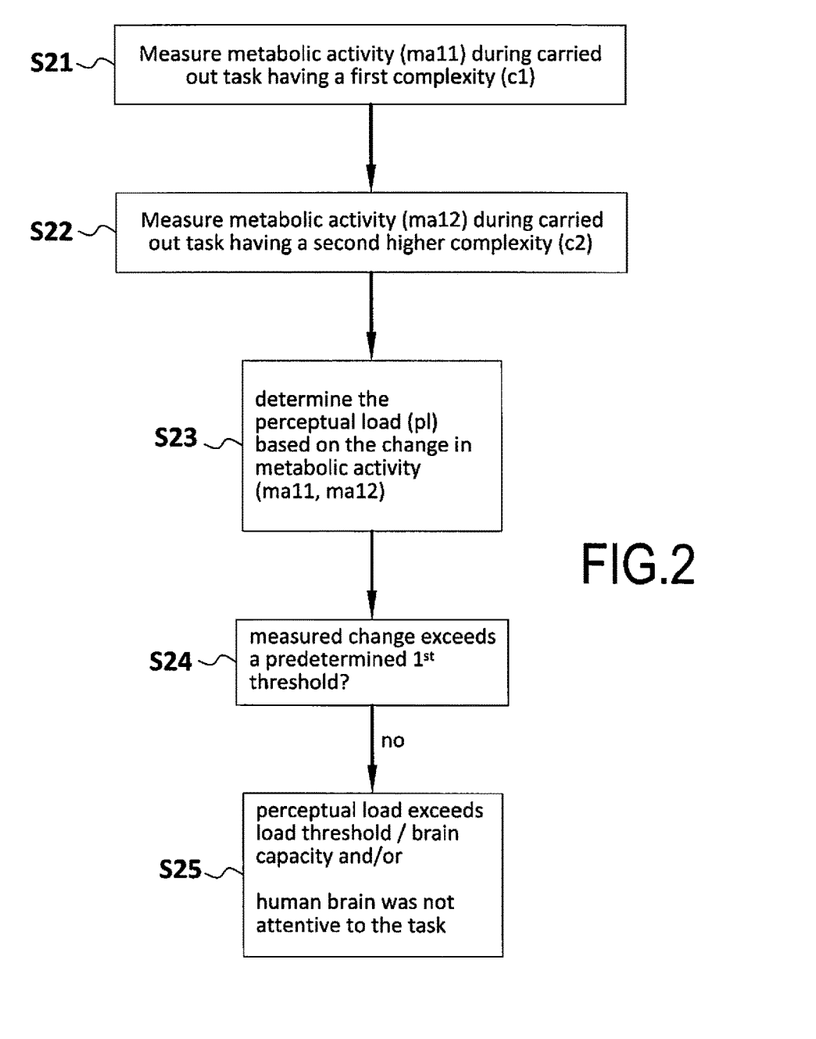
FIG. 2 shows a schematic flow chart illustrating an exemplary method of determining the perceptual load according to embodiments of the present disclosure.

FIG. 2 shows a schematic flow chart illustrating an exemplary method of determining the perceptual load according to embodiments of the present disclosure.

In step S21 the metabolic activity ma11 of a human brain is measured during a task having a first complexity level c1 carried out by the human. In more detail, a human may be exposed to a stimulus of a first type and may be instructed to perceive the stimulus of the first type and in response thereto to carry out a predetermined task. Due to the task to carried out a perceptual load is induced in the human brain which causes a measurable metabolic activity.

In step S22, the procedure of step S21 is repeated, however with an increased complexity level c2 of the task. Said increase complexity may be controlled by a correspondingly more complex stimulus of the first type. Again, in step S22 the metabolic activity ma12 is measured.

The steps S21 and S22 may also have another order. It is also possible that steps S21 and S22 are repeated for several times, and e.g. mean values of the respective measurements are determined.

In step S23 the perceptual load (pl) of the human brain is determined (or estimated) based on the change in metabolic activity between the measured metabolic activity ma11 in step S21 and the measured metabolic activity ma12 in step S22. Generally, a significant change indicates that the human brain is still able to perceive and/or keep control of the task.

In step S24 it may be determined, whether the (measured) change exceeds a predetermined $1^{st}$ threshold.

If it does not, it is determined in step S25 that the perceptual load exceeds a predefined load threshold, e.g. a predetermined value or a maximum brain capacity. It may be also followed that the human brain was not attentive to the task (e.g. not any more due to the increased complexity). For example, in case the method is used in a vehicle and the related task is a driving task, an automated driving system may take over the driving control.

Figure 3:
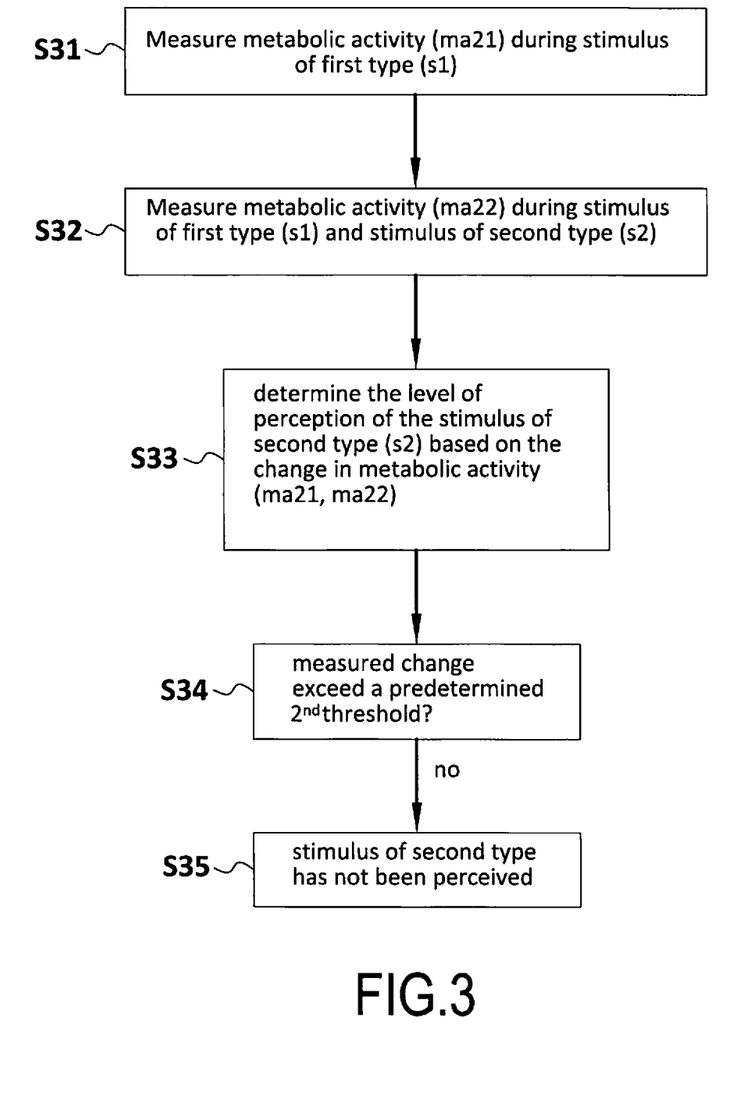
FIG. 3 shows a schematic flow chart illustrating an exemplary method of determining the level of perception according to embodiments of the present disclosure.

FIG. 3 shows a schematic flow chart illustrating an exemplary method of determining the level of perception of an (unattended) stimulus of a second type according to embodiments of the present disclosure.

In step S31 the metabolic activity ma21 is measured during a stimulus of a first type. In more detail, a human is exposed to the stimulus of the first type s1 and is instructed to perceive the stimulus of the first type and in response thereto to carry out a predetermined task. Due to the stimulus perception and the task to be carried out a perceptual load is induced in the human brain which causes a measurable metabolic activity.

In step S32, the procedure of step S31 is repeated, however with additionally exposing the human to a stimulus of a second type s2, desirably at the same time as the stimulus of the first type s1.

The stimulus of the second type is desirably not related to any predetermined task which is to be carried out by the human, or may be only weakly related or may be related as a secondary stimulus to the primary task stimuli. In other words, the stimulus of the second type may be perceived and therefore noticed by the human without implying any additional action to be taken than the task related to the stimulus first stimulus. The first sensor may namely be used to determine whether the stimulus was attended or not. The method may be applied to a stimulus that needs to be attended too but with a secondary level of importance to the task-related stimuli.

Again, in step S32 the metabolic activity ma22 is measured, which is however now not only influenced by the stimulus of the first type (as ma21 in step S31) but additionally by the stimulus of the second type s2.

The steps S31 and S32 may also have another order. It is also possible that steps S31 and S32 are repeated for several times, and e.g. mean values of the respective measurements are determined.

In step S33 the level of perception of the stimulus of the second type (s2) is determined (or estimated) based on the change in metabolic activity between the measured metabolic activity ma21 in step S31 and the measured metabolic activity ma22 in step S32. Generally, a reduced change indicates that the level of perception of the stimulus of the second type is reduced. In other words, an increased change indicates that the human brain still is able to perceive the additional unattended stimulus of the second type.

In step S34 it may be determined, whether the (measured) change exceed a predetermined $2^{st}$ threshold.

If it does not, it is determined in step S35 that stimulus of the second has not been perceived, or at least has not been perceived sufficiently. For example, in case the method is used in a vehicle and the stimulus of the second type is an identified potentially dangerous event in the driving scene, a warning signal may be activated or an automated driving system may take over the driving control as a precautionary measure.

Figure 4:
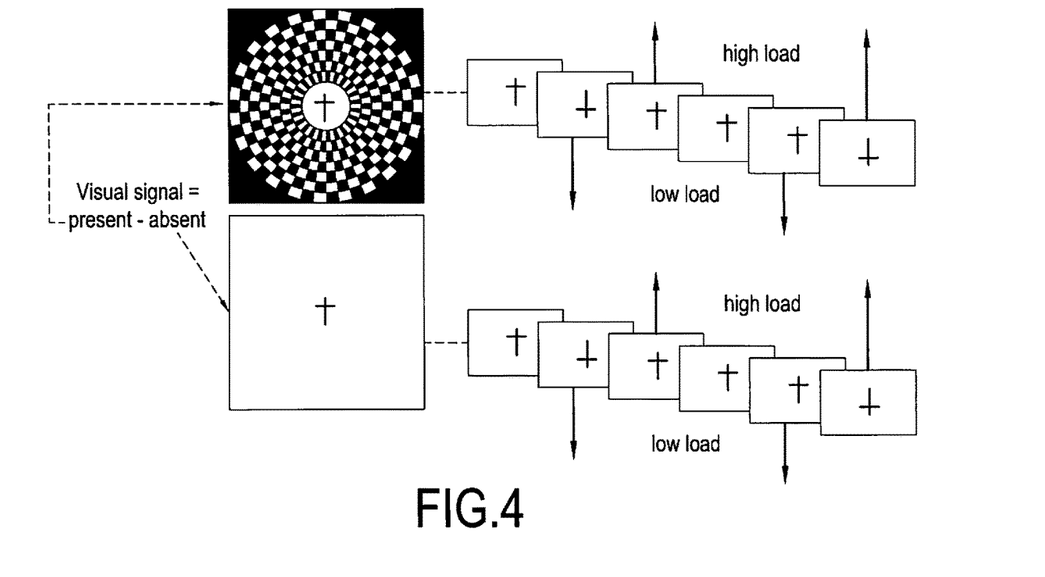
FIG. 4 shows a schematic representation of exemplary stimuli according to embodiments of the present disclosure.

FIG. 4 shows a schematic representation of exemplary stimuli according to embodiments of the present disclosure. In particular, FIG. 4 shows stimuli used in an experiment, where participants are exposed to different stimuli of a first type in the form of subsequently appearing crosses of different colors and shapes and to stimuli of the second type in the form of a randomly appearing or e.g. appearing on every nth stimulus (n>1) checkerboard.

In more detail, participants are presented with a rapid stream of coloured crosses with 2 different orientations (upright/inverted). During high load blocks (see blocks with indicated by an upward arrow) the targets are defined by a conjunction of orientation and colour, whereas during low load (see blocks with indicated by a downward arrow) the targets are defined by colour alone. Note that the visual stimulation may be hence the same in both conditions and only the target instructions may vary.

Each block has a duration of e.g. 25 seconds, followed by a 25 second rest period. On half of the trials a full-field flickering checkerboard is present in the periphery, which participants are instructed to ignore.

To test the hypothesis that the change in the oxCCO signal in response to the unattended stimulus is modulated by the level of load a repeated measures ANOVA (analysis of variance) with the two factors load and distractor presence (i.e. presence of the stimulus of the second type) may be performed for each region of interest (ROI).

Figure 5:
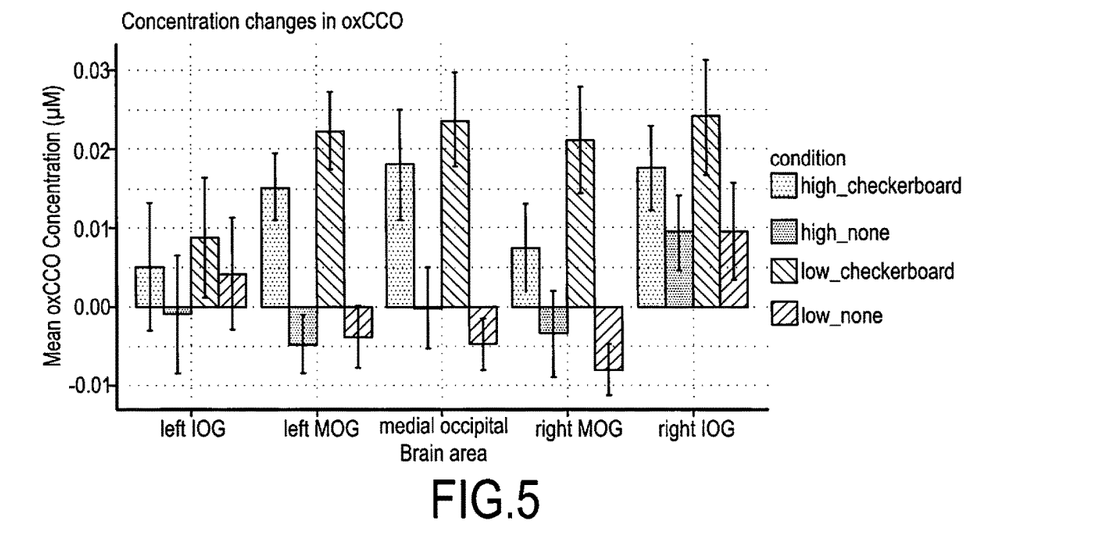
FIG. 5 shows a diagram with exemplary levels of measured metabolic activity according to embodiments of the present disclosure.

FIG. 5 shows a diagram with exemplary levels of measured metabolic activity according to embodiments of the present disclosure. In particular, FIG. 5 shows four means (i.e. test results) for each brain area. These correspond to the high vs low load conditions each with and without the additional stimulus of the second type (i.e. the checkerboard). In two areas (medial occipital and right MOG) the relative increase from the checkerboard absent condition to the checkerboard present condition is significantly larger under low perceptual load than high perceptual load (i.e. the checkerboard is perceived more strongly during the easy task).

Figure 6:
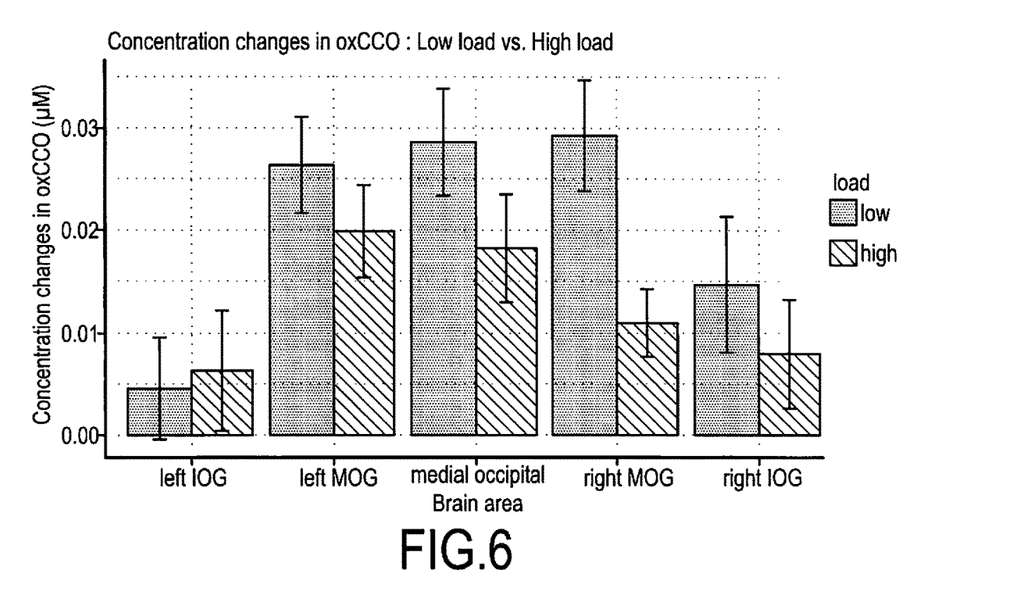
FIG. 6 shows a diagram with exemplary changes of measured metabolic activity due to an added stimulus of a second type according to embodiments of the present disclosure.

FIG. 6 shows a diagram with exemplary changes of measured metabolic activity due to an added stimulus of a second type according to embodiments of the present disclosure. In comparison to FIG. 5, FIG. 6 shows just the relative difference between the checkerboard present and absent conditions for high and low load (i.e. the subtraction of checkerboard absent values from checkerboard present values).

In particular, FIG. 6 shows a comparison of oxCCO concentration changes in relation to the presence of the stimulus of the second type (presence minus absence) under high and low perceptual load conditions: Significantly higher signal increases in response to the presence of a checkerboard during low load than high load were found in the medial occipital lobe and the right medial occipital gyrus. Errorbars represent the standard error of the mean.

The interaction between load and distractor presence (i.e. the stimulus of the first and second type) is significant in the medial occipital lobe ($F(1,12)=9.18$, $p=0.010$) and the right MOG ($F(1,9)=10.39$, $p=0.010$). The direction of this interaction was as predicted: For both ROIs the difference in signal change between present versus absent conditions was larger in low load (medial occipital lobe: $M=0.029$ µM, $SD=0.019$; right MOG: $M=0.029$ µM, $SD=0.018$) than in high load (medial occipital lobe: $M=0.018$ µM, $SD=0.019$; right MOG: $M=0.011$ µM, $SD=0.011$). Post-hoc paired t tests confirmed that there was a simple main effect of distractor presence in low load (medial occipital lobe: $t(12)=5.52$, $p<0.001$; right MOG: $t(9)=5.29$, $p=0.001$) as well as high load (medial occipital lobe: $t(12)=3.40$, $p=0.005$; right MOG: $t(9)=3.20$, $p=0.011$) in both ROIs. The trend of an attenuated oxCCO signal for the presence vs. absence of the distractor was consistent across all other ROIs apart from the left IOG (see FIG. 5). This indicates that metabolic activity related to the presence of a distractor is reduced under conditions of high perceptual load compared to low load. To the knowledge of the inventors this is the first direct evidence that load-dependent attentional modulations impact on cerebral metabolism in the visual cortex.

This result is in line with previous fMRI findings that have used blood oxygen level dependent (BOLD) signals to measure the load modulation of neural responses in the visual cortex responses (Rees et al., 1997; Schwartz et al., 2005; Torralbo et al., 2016). However, these previous findings were not directly related to cerebral energy consumption: The BOLD signal capitalises on the paramagnetic properties of HHb. During neural activity, the concentration of HHb decreases due to a complex interplay of changes in cerebral blood flow, cerebral blood volume, and cellular metabolism. The significantly larger changes in blood flow are not a direct consequence of the increased energy demand, but triggered by glutamatergic signalling. Importantly, since the coupling between them is variable over space and time and it is affected by neural activation, the two processes should not be equated with each other. The BOLD signal which measures the level of HHb is therefore not suitable to test a hypothesis that is specific to cerebral metabolism The results as described in the present disclosure accommodate a recent finding by Moradi et al. (2012) in which they used fMRI to measure the BOLD signal as well as cerebral blood flow (CBF) in order to mathematically estimate the cerebral metabolic rate of oxygen ($CMRO_2$) during conditions of attended and unattended viewing of a peripheral checkerboard stimulus. The unattended condition consisted of a central n-back task, while the attended condition required the participants to covertly shift their attention to the surrounding checkerboard and detect changes in brightness while fixating the centre of the screen. However, eye movements were not controlled for in this experiment and the difference between attended and unattended conditions could be due to a stronger visual signal caused by fixation of the checkerboard during the attended condition (as opposed to covert shifts of attention).

In the present disclosure, as described above in context of FIG. 4 to 6, participants had to perform a task at the centre of the screen during high load ('unattended') and low load ('attended') conditions, and the checkerboard distractor was irrelevant in both conditions. Furthermore, the fast rate of stimulus presentation ensured that this fixation was upheld.

Load theory's limited capacity model of perceptual processing is supported by the results, as described above in context of FIG. 4 to 6, which focus on metabolism as a possible physiological correlate for the capacity limitation of perceptual processing. The overall energy consumption of the brain remains relatively constant independent of mental states. However, neural spiking is metabolically very expensive. This has led to the proposal of a sparse coding model where resources are saved by using only very few active neurons to represent relevant information. the present disclosure is in support of such models since it shows that metabolic activity is significantly attenuated under conditions where enhanced processing of other stimuli is necessary due to task demands. In particular, the metabolic resources saved by diminishing representations of task-irrelevant stimuli under high load conditions are indeed used to improve the representations of the attended, task-relevant stimuli.

In conclusion, the results, as described above in context of FIG. 4 to 6, show that for task-irrelevant stimuli cerebral metabolism in the striate and extrastriate cortex is significantly attenuated during conditions of high compared to low perceptual load. These attention induced load-dependent changes of cellular metabolism are explained within the framework of the perceptual load theory (cf. e.g. Lavie, Nilli; Tsal, Yehoshua (1994). "Perceptual load as a major determinant of the locus of selection in visual attention", Perception and Psychophysics, 56 (2): 183-197, Lavie, N. (1995). Perceptual load as a necessary condition for selective attention. Journal of Experimental Psychology: Human Perception and Performance, 21, 451-468, Lavie, N. (2005) Distracted and confused?: selective attention under load. Trends in Cognitive Sciences, 9, 75-82, and Lavie, N., Beck, D. M. & Konstantinou, N. (2014). Blinded by the load: attention, awareness and the role of perceptual load. Philosophical Transactions of the Royal Society B: Biological Sciences, 369: 20130205) and accommodate a wealth of neuroimaging findings that found reduced BOLD responses (Rees et al., 1997; Schwartz et al., 2005; Torralbo et al., 2016), neural excitability (Muggleton et al., 2008) and neural field potentials for task-irrelevant stimuli under high load conditions. Importantly, it a demonstration that metabolism is directly affected by load and therefore may be the neural correlate of the capacity limitations outlined in load theory. Furthermore, the present disclosure demonstrates how multichannel, broadband fNIRS may be an advantageous neuroimaging tool for, since it allows the differentiation between vascular and metabolic factors which are not possible in measures such as the BOLD signal.

Figure 7:
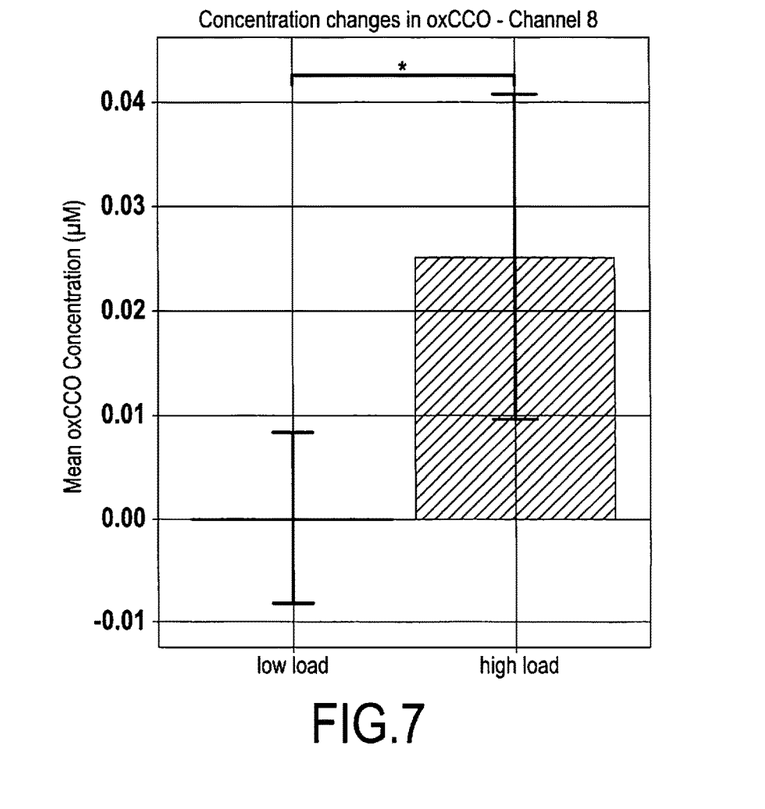
FIG. 7 shows a diagram with exemplary changes of measured metabolic activity due to an increased complexity of a task according to embodiments of the present disclosure.

FIG. 7 shows a diagram with exemplary changes of measured metabolic activity due to a changed perceptual load of a task carried out by the human. The task was the same as in FIG. 4 but the crosses were larger and patterend. In particular, FIG. 7 shows a Comparison of oxCCO concentration changes between a low load task and high load in the absence of the flickering checkerboard (the stimulus of the second type): Significantly higher signal increases in response to the increased perceptual load of the task were found. Errorbars represent the standard error of the mean.

In the present example, Channel 8 is used for measurement. The fNIRS system has measurement channels that lie between each source and detector. In the present exemplary case, Channel 8 refers to a location in the occipital lobe (Left medial occipital gyrus) in which the measured changes between high and low load reached statistical significance. Hence, desirably the measurement is taken at the occipital lobe.

Throughout the description, including the claims, the term "comprising a" should be understood as being synonymous with "comprising at least one" unless otherwise stated. In addition, any range set forth in the description, including the claims should be understood as including its end value(s) unless otherwise stated. Specific values for described elements should be understood to be within accepted manufacturing or industry tolerances known to one of skill in the art, and any use of the terms "substantially" and/or "approximately" and/or "generally" should be understood to mean falling within such accepted tolerances.

Although the present disclosure herein has been described with reference to particular embodiments, it is to be understood that these embodiments are merely illustrative of the principles and applications of the present disclosure.

It is intended that the specification and examples be considered as exemplary only, with a true scope of the disclosure being indicated by the following claims.

The invention claimed is:

1. A method of determining perceptual load of a human brain, the perceptual load being induced by a predetermined task carried out by the human, the method comprising:
    measuring a metabolic activity of the human brain with a functional near-infrared spectroscopy sensor device while the predetermined task is carried out, wherein the predetermined task comprises a varying complexity inducing a correspondingly varying perceptual load,
    determining the perceptual load as a function of a measured change in metabolic activity, and
    determining that the human brain was not attentive to the predetermined task in case the complexity decreases and at the same time the measured change in metabolic activity does not decrease below a first upper threshold or does not exceed a predetermined first lower threshold.

2. The method according to claim 1, further comprising
    determining that the human brain is still able to perceive and/or keep control of the task in case the metabolic activity is changing for more than a predetermined amount; and
    determining that the perceptual load induced by the predetermined task exceeds a perceptual load threshold and/or that the human brain was not attentive to the task in case the complexity increases and at the same time the measured change in metabolic activity does not exceed a predetermined first upper threshold.

3. A method of determining a level of perception of a stimulus of a second type by a human brain, the method comprising:
    period exposing the human brain to a predetermined stimulus of a first type in a first time period, in response to which the human carries out a predetermined task, thereby inducing a perceptual load in the human brain,
    exposing the human brain to a predetermined stimulus of the first type and a predetermined stimulus of a second type perceivable by the human brain in a second time period,
    measuring a metabolic activity of the human brain with a functional near-infrared spectroscopy sensor device in the first and the second time period, wherein the sensor device is a broadband functional near-infrared spectroscopy sensor device configured to sense in a range of 650 nm to 900 nm, and
    determining the level of perception of the stimulus of the second type as a function of a measured change in metabolic activity in the second time period in relation to the first time period.

4. The method according to claim 3, wherein
the first type is a task-primary type, and the second type is a task-secondary type.

5. The method according to claim 3, further comprising
    determining that the level of perception of the stimulus of the second type exceeds a predetermined minimum perception level in case the measured change in metabolic activity in the second time period in relation to the first time period exceeds a predetermined second upper threshold, and/or
    determining that the human brain does not perceive the stimulus of the second type and/or that the human brain did not attend to the stimulus of the second type in case the measured change in metabolic activity in the second time period in relation to the first time period does not exceed the second upper predetermined threshold.

6. The method according to claim 3, comprising at least one of:
    generating the predetermined task to be carried out by the human; and
    sensing the predetermined task carried out by the human.

7. The method according to claim 3, wherein
the predetermined stimulus of the first type comprises a driving scene, and
the predetermined task comprises a driving task.

8. The method according to claim 3, wherein
the stimulus of the first type is attended by the human when carrying out the task, and/or
the stimulus of the second type is not predetermined by the task such that the stimulus of the second type is an unattended stimulus for the human when carrying out the task.

9. The method according to claim 3, wherein
the stimuli of the first type are variable such that complexity of the predetermined task varies correspondingly.

10. A system for determining perceptual load of a human brain, the system comprising:
a functional near-infrared spectroscopy sensor device configured to measure a change in metabolic activity of the human brain, and
a control device configured to determine the perceptual load based on the measured change in metabolic activity, wherein
the perceptual load is induced by a predetermined task carried out by the human,
the predetermined task comprises a varying complexity inducing a correspondingly varying perceptual load, and
the control device is configured to determine that the human brain was not attentive to the task in case the complexity decreases and at the same time the measured change in metabolic activity does not decrease below a predetermined first upper threshold or does not exceed a predetermined first lower threshold.

11. The system according to claim 10, wherein
the perceptual load is induced by a predetermined task carried out by the human, and/or
the system comprises:
a generating and/or sensing device configured to:
generate a predetermined task to be carried out by the human and/or sense a predetermined task carried out by the human.

12. A system for determining a level of perception of a stimulus by a human brain, the system comprising:
a generating and/or sensing device configured to:
in a first time period and in a second time period generate a predetermined task to be carried out by the human and/or sense a predetermined task carried out by the human,
in the second time period generate and/or sense a predetermined stimulus perceivable by the human brain,
a broadband functional near-infrared spectroscopy sensor device configured to sense in a range of 650 nm to 900 nm and to measure a metabolic activity of the human brain in the first time period and the second time period, and
a control device configured to determine the level of perception of the stimulus as a function of a measured change in metabolic activity in the second time period in relation to the first time period.

13. The system according to claim 12, wherein
the broadband functional near-infrared spectroscopy sensor device is configured to measure redox state changes of a mitochondrial enzyme indicative of cellular oxygen metabolism.

14. The system according to claim 13, wherein
the mitochondrial enzyme indicative of cellular oxygen metabolism is cytochrome c oxidase.

15. The system according to claim 12, wherein
measured changes in metabolic activity indicate an increase in energy consumption during neural responses of the human brain.

16. The system according to claim 12, wherein
the broadband functional near-infrared spectroscopy sensor device is further configured to measure concentration changes of oxygenated haemoglobin and/or of deoxygenated haemoglobin.

17. The system according to claim 12, wherein
the control device is configured to pre-select regions of interest of the brain based on concentration changes of oxygenated haemoglobin and/or of deoxygenated haemoglobin that are measured, and determine perceptual load based on the measured changes in metabolic activity in the pre-select regions of interest of the brain.

18. The system according to claim 12, wherein
the broadband functional near-infrared spectroscopy sensor device is configured to measure changes in metabolic activity in the medial occipital lobe and/or the right medial occipital gyrus of the human brain, and
the control device is configured to determine perceptual load based on the measured changes in metabolic activity in the medial occipital lobe and/or the right medial occipital gyrus.

19. The system according to claim 12, wherein
the sensor device comprises a plurality of sources and a plurality of detectors configured to provide a plurality of measurement channels across the occipital lobe of the brain.

20. The system according to claim 12, wherein
the measurement channels are spread over outer extents of the primary visual cortex and/or across extrastriate areas of the brain.

21. The system according to claim 12, wherein
the measurement channels are grouped into a plurality of regions of interest of the brain including the left/right inferior occipital gyrus, the left/right middle occipital gyrus, and/or the medial occipital lobe.

* * * * *